(12) United States Patent
Michelson

(10) Patent No.: US 6,175,962 B1
(45) Date of Patent: *Jan. 23, 2001

(54) SURGICAL GLOVE

(76) Inventor: Gary Karlin Michelson, 438 Sherman Canal, Venice, CA (US) 90291

( * ) Notice: Under 35 U.S.C. 154(b), the term of this patent shall be extended for 0 days.

This patent is subject to a terminal disclaimer.

(21) Appl. No.: 07/919,844

(22) Filed: Oct. 26, 1992

Related U.S. Application Data

(63) Continuation of application No. 07/258,552, filed on Oct. 17, 1988, now abandoned.

(51) Int. Cl.⁷ .............................. A41D 13/10; A41D 19/00
(52) U.S. Cl. ................................. 2/161.7; 2/168; 128/918
(58) Field of Search .................... 2/161 R, 163, 2/161.7, 168, 16, 169, 164, 159; 128/844, 842, 917, 918; 604/349, 353; 428/913, 916, 323

(56) References Cited

U.S. PATENT DOCUMENTS

| | | | |
|---|---|---|---|
| 3,633,216 | * 1/1972 | Schonholtz | 2/168 |
| 3,637,411 | * 1/1972 | Agostinelli | 2/168 |
| 3,675,654 | 7/1972 | Baker et al. | 604/361 |
| 3,731,685 | * 5/1973 | Eidus | 604/361 |
| 4,742,578 | * 5/1988 | Seid | 2/167 |
| 4,743,238 | * 5/1988 | Colon et al. | 604/361 |
| 4,843,014 | 6/1989 | Cukier | 2/168 X |
| 4,931,051 | * 6/1990 | Castello | 604/361 |
| 4,935,260 | * 6/1990 | Shlenker | 128/844 |
| 4,992,335 | * 2/1991 | Guerra et al. | 2/159 |
| 5,017,427 | * 5/1991 | Machida et al. | 2/168 |
| 5,024,852 | * 6/1991 | Busnel et al. | 128/844 |
| 5,224,221 | * 7/1993 | Richardson et al. | 2/168 |
| 5,230,350 | * 7/1993 | Fentress | 604/361 |

FOREIGN PATENT DOCUMENTS

| | | | |
|---|---|---|---|
| 3925938 | * 4/1990 | (DE) | 2/168 |
| 0300814 | * 1/1989 | (EP) | 2/168 |
| 2208358 | * 3/1989 | (GB) | 2/167 |

* cited by examiner

*Primary Examiner*—Amy B. Vanatta
(74) *Attorney, Agent, or Firm*—Martin & Ferraro, LLP

(57) ABSTRACT

A puncture resistant surgical glove which is sterilizable, supple, and contains a leak detection mechanism for the purpose of protecting the wearer from the biohazard of microorganism inoculation via hand skin puncture is disclosed. A condom having a leak detection mechanism is also disclosed.

146 Claims, 5 Drawing Sheets

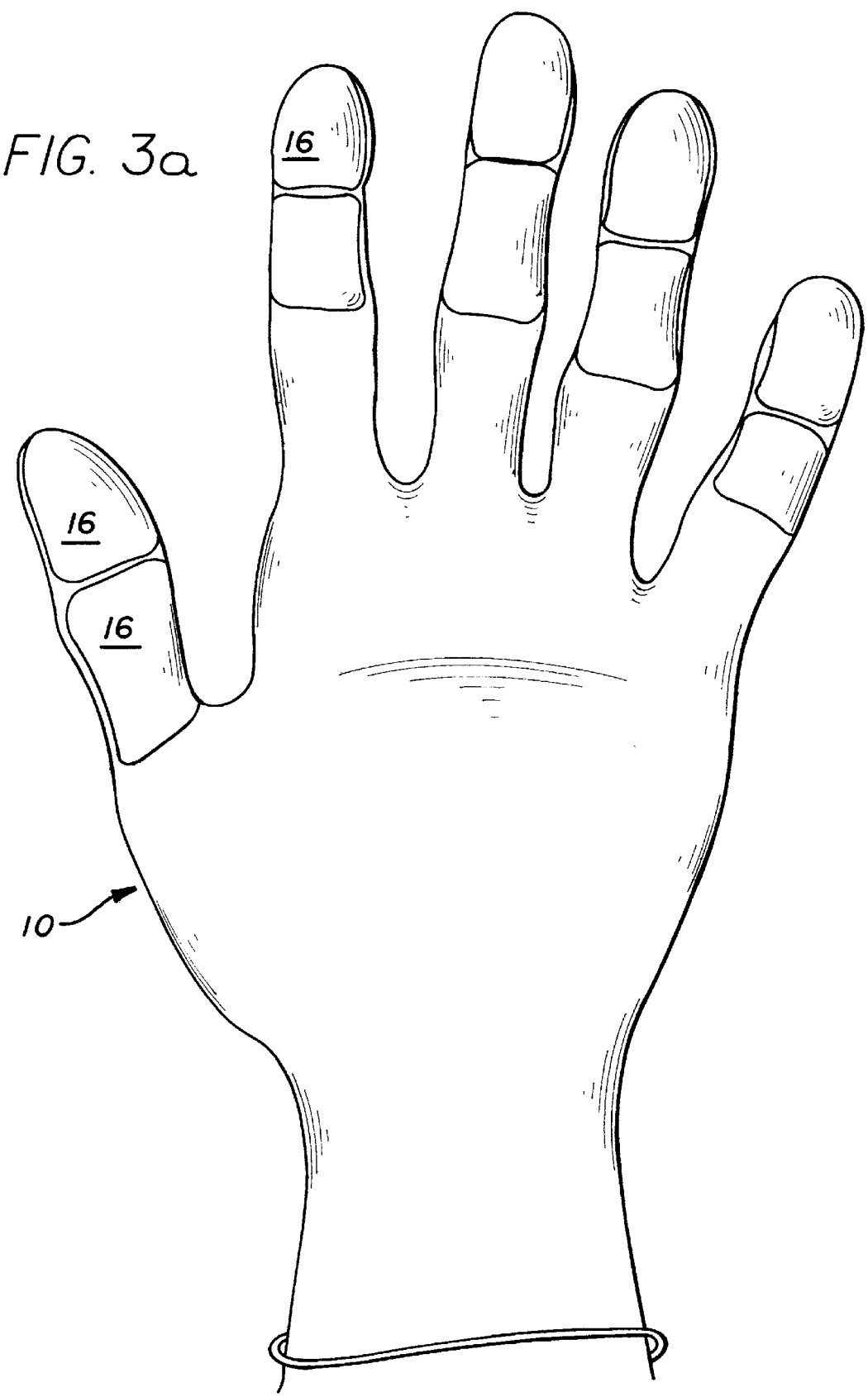

SURGICAL GLOVE

This application is a continuation of application Ser. No. 07/258,552, filed Oct. 17, 1988 now abandoned.

BACKGROUND

The use of flexible latex gloves by surgical personnel began as a protection against the commonly used antiseptic carbolic acid. However, with advances in microbiology the wearing of gloves during surgery to prevent wound sepsis became well established. Because of the relatively new situation which has arisen in regard to virally transmitted illnesses, such as Acquired Immune Deficiency Syndrome (AIDS) and hepatitis, there now is significant concern about protecting the surgical personnel from contamination by the patient.

Almost all surgical gloves are presently made of latex. Most surgical personnel now wear two pairs of gloves simultaneously in the hope of obtaining some degree of enhanced protection. Numerous studies have shown that people's hands, including those of medical personnel, frequently contain microcracks in the skin which could serve as entrance sites for live viruses. The use of two gloves on each hand provides some enhancement of safety to the wearer as a hole in the outer glove will not result in the patient's blood contacting the wearer's skin as long as the inner glove remains intact. However, it is quite possible, due to either faulty manufacturing or during the operation, to have holes through both the outer and inner gloves. Since surgical gloves are usually bloody, the user would not be aware that such holes exist until after the surgery is completed and the gloves are removed.

The greatest threat to the surgeon from contamination is posed by a needle puncture as it almost virtually guarantees that both gloves and the wearer's skin will be punctured simultaneously. Since the needle has usually passed through the patient's tissues, inoculation with the patient's blood and any viruses which it may contain will in fact occur. Since there is a loss of sensitivity to the surgeon when wearing two gloves, the likelihood of this accidental puncturing is increased.

While puncture resistant gloves made of fine metal mesh, such as Kevlar or Kevlar and wire, are known, these prior gloves have many disadvantages. They are incapable of stopping a fine needle puncture, are not waterproof, and they lack the pliancy needed to function as surgical gloves.

THE PRESENT INVENTION

The present invention consists of a latex surgical glove, or equivalent, reinforced over the high risk areas, with thin segments of a hard material which is inpenetrable by a needle or blade such as plastic, including Lexan, polypropylene, polycarbonate, PVC, etc. or any other equally thin, pliant and puncture proof material. Such segments may be applied to the outer surface of a single or double layered glove, or may be permanently sealed between two layers of the gloves.

In the preferred embodiment, an iodinated coating is applied between the two layers of latex and a fine dusting of cornstarch is applied to the interior of the inner glove only. The cornstarch facilitates the donning of the gloves acting as a dry lubricant. As is the custom, the surgeon would rinse the outer glove after donning to moisten its outer surface. If, as a result of a defect in manufacturing, packaging, or as a degradative change from prolonged storage, both of the gloves are already perforated at the time of application, then fluid passing through the iodinated layer to the cornstarch dusting would cause a ninhydrin reaction to occur from the mixing of the two chemicals with fluid. The mixing will produce a bright blue purple spot to appear, thus alerting the wearer immediately to the presence of a glove puncture. While iodine and starch are described, the use of other chemicals that cause a color change when mixed could be utilized as well.

Furthermore, both chemical agents could be mixed and placed in a dry form between the two layers of the glove so that the color change would occur when fluid, such as blood, was introduced through an opening in the outer layer only, rather than through both layers of the glove. This would alert the wearer to a puncture of only the outer glove, while the inner glove still remained intact. Just as the detection mechanism will indicate a glove defect immediately upon donning when wetted, the same mechanism will also detect a glove rupture occurring any time thereafter and by the means just described, when mixed with blood.

While the above described gloves would be for medical and scientific personnel requiring sterilizable and highly pliant gloves, other applications of the innovative concept may be employed. For example, dual layered condoms could be made so that wetting of the condom, would reveal any holes in the outer layer, and more importantly holes in both of the layers.

OBJECTS OF THE INVENTION

It is an object of the present invention to provide for an improved surgical glove that is more resistant to needle punctures and thus, safer to the patient and the wearer.

It is another object of the present invention to provide for an improved surgical glove that provides the advantages of a double glove in a single laminated form.

It is still another object of the present invention to provide for an improved surgical glove that is capable of detecting and indicating the integrity of either the outer of two layers or both layers of the glove throughout the surgical procedure.

It is still another object of the present invention to provide for an improved condom that would reveal any leaks, either before or after use.

These and other objects of the present invention will be apparent from a review of the following specification and accompanying drawings.

BRIEF DESCRIPTION OF THE DRAWINGS

FIG. 3A is an alternative embodiment of the glove of the present invention.

DETAILED DESCRIPTION OF THE DRAWINGS

Figure 1:
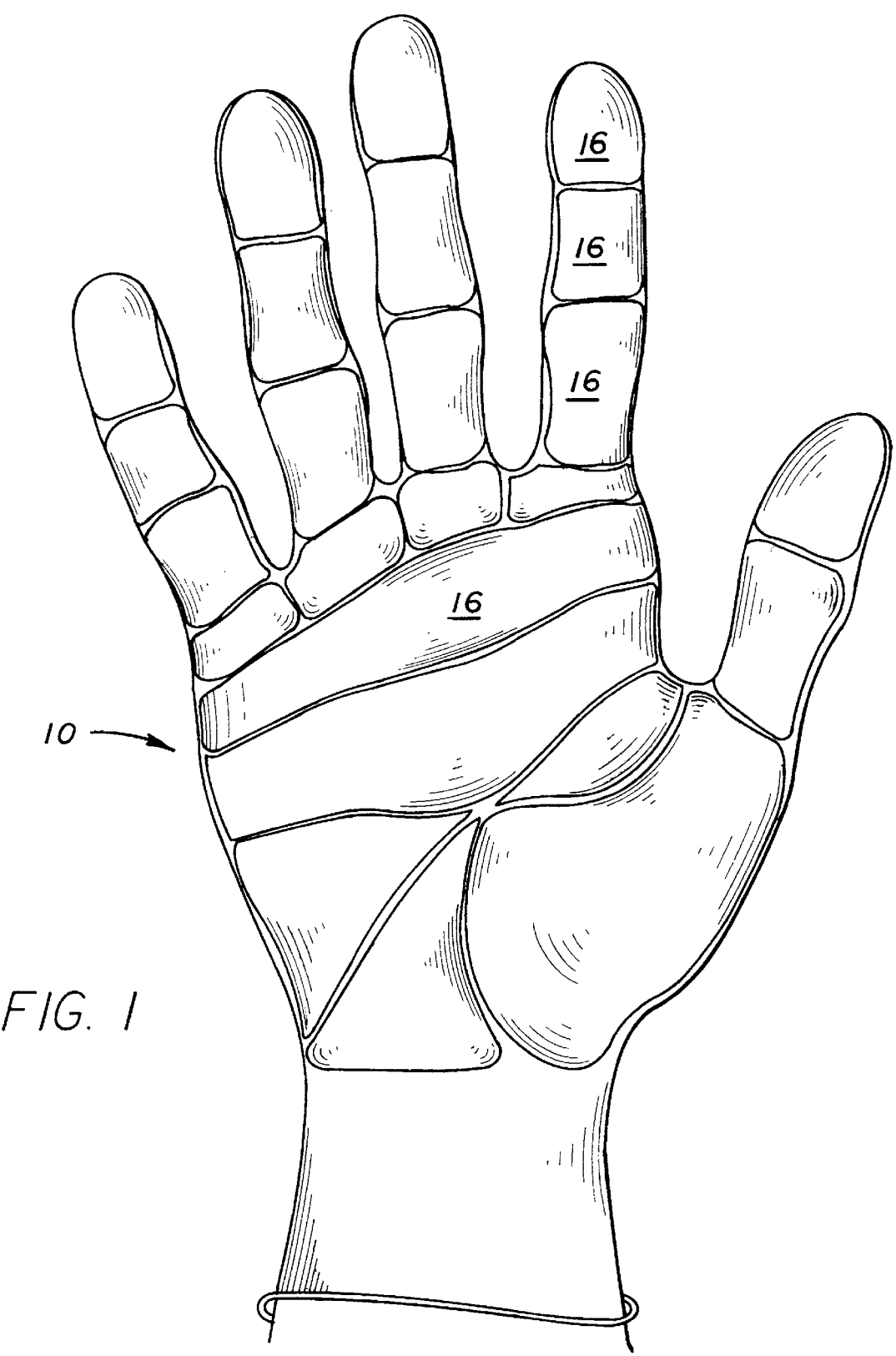
FIG. 1 is a front view of the glove of the present invention showing reinforced sections.
Figure 2:
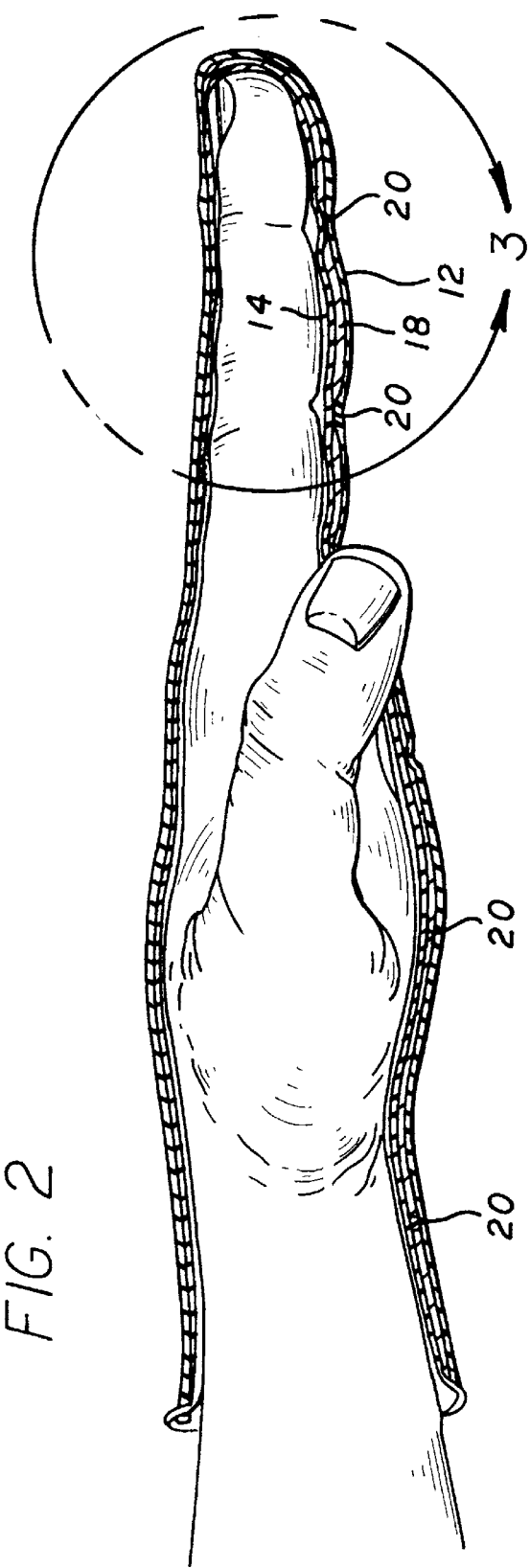
FIG. 2 is a side sectional view of the glove of the present invention.
Figure 3:
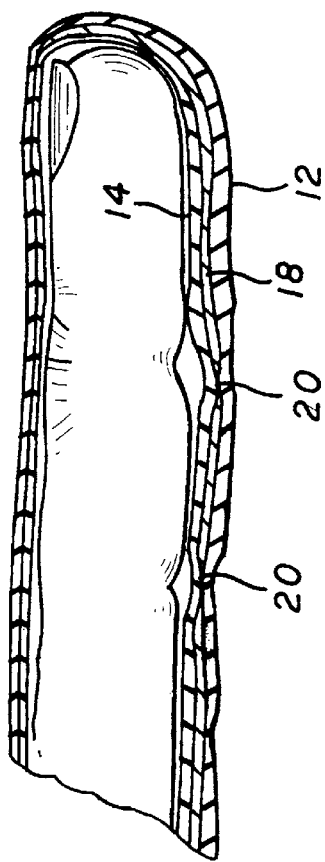
FIG. 3 is an expanded partial sectional view of a finger of the glove of FIG. 2.

Referring to FIGS. 1–3, the puncture resistant glove of the present invention is shown. The glove 10 comprises an inner layer 14 and an outer layer 12 of flexible plastic material, such as latex.

Segments 16 of a generally solid impermeable material such as hard plastic or thin metal, are fitted between the first layer 12 and the second layer 14. The segments 16 are slightly smaller in size than the joints of the fingers and palm.

The segments 16 are held in place either by adhesively applying them in place to the inner or outer layers of the glove 10, or, as in the preferred embodiment, by forming a chamber 18, between the two layers of the glove by sealing a portion of the first layer 12 to the second layer 14 at the creases of the glove, to form a seal 20. Other conventional methods of bonding the segments to the glove may be used.

In FIG. 1, a plurality of segments 16 along the finger joints, finger tips and along the palms are shown. Depending on the type of operation being performed, the segments may be placed in less than all possible locations, such as shown in the alternative embodiment FIG. 3a, where segments 16 are located only along the finger tips and are not located along the palm portion of the glove.

Figure 4:
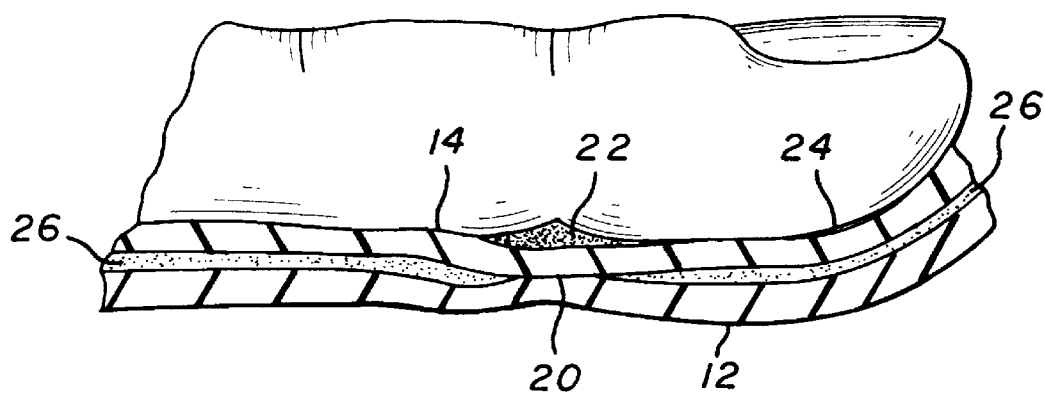
FIGS. 4, 5 and 6 are alternative embodiments of the present invention employing color indicating means.
Figure 5:
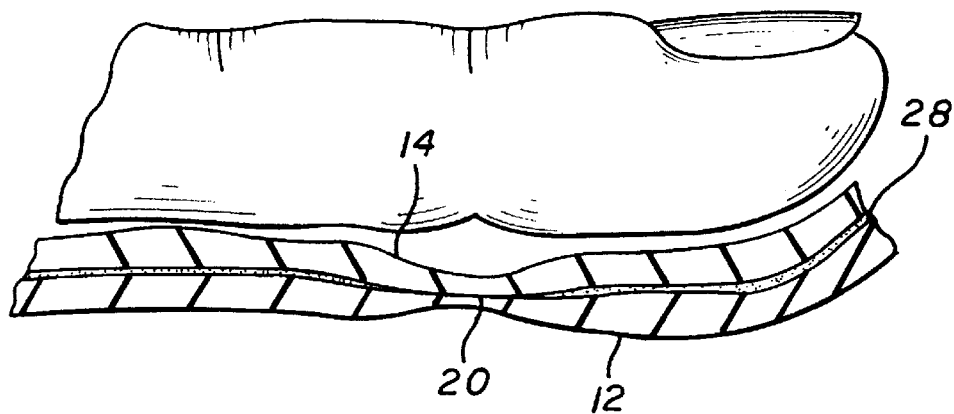
Figure 6:
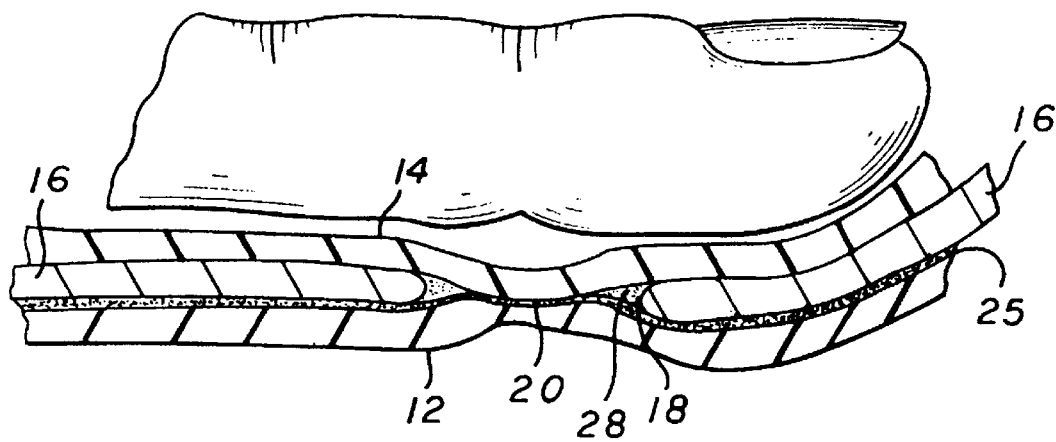

Referring to FIG. 4–6 alternative embodiments of the present invention are shown employing indicating means for indicating an opening in the inner layers and/or the outer layers of the gloves.

In FIG. 4 a cornstarch 22 or similar chemical is applied to the inside surface 24 of the inner layer 14 of the glove 10. An iodinized material 26 or similar chemical substance is applied between the inner layer 14 and the outer layer 12. The inner layer 14 and the outer layer 12 are joined at seals 20 to keep the iodinized material uniformly distributed. Puncture of the inner and outer layers will cause the cornstarch 22 and iodinized material 26, when mixed with the blood, to have a ninhydrin reaction, resulting in a bright contrasting color to the latex in the vicinity of the puncture.

In FIG. 5, an alternative embodiment of the glove is shown in which puncture resistant segments are not employed. A chemical mixture 28 comprising the cornstarch 22 and the iodinized material 26 is placed in the space between the inner layer 14 and the outer layer 12. The chemical mixture 28 may be first mixed and then sprayed as a layer to facilitate manufacturing.

An opening in just the outer layer 12 and not the inner layer 14, which introduces fluid such as blood, would result in the creation of a bright contrasting color in the vicinity of the opening.

In FIG. 6, the use of the puncture proof segments 16 and the mixture 28 is shown. The mixture 28 is placed at the locations 18 where there is not puncture proof segments 16. A seal 20 is shown to retain the segments in place. Additionally, adhesive 25 is shown for holding the segment 16 in place. In the event of a puncture at the joint of the finger in the vicinity of the seal 20, the color indicating means will be activated.

Figure 7:
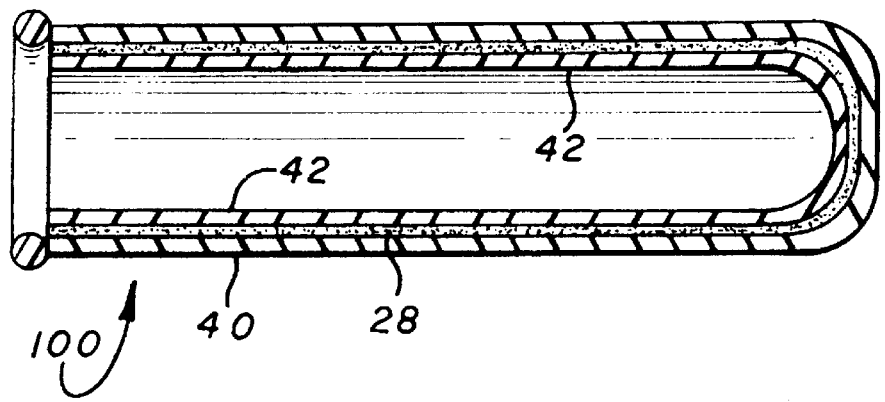
FIG. 7 is an alternative application of the invention in a condom.

While the invention has been described in association with preferred embodiments, in the form of a glove, it is recognized that other forms of the invention may be made that are not gloves, but would also indicate the lack of integrity of a material desired to be protected from liquids. Referring to FIG. 7, one other such use shown in association with a condom 100. The mixture 28 is present between the inner layer 42 and the outer layer 40. The passing of fluid through the inner layer 42 of the condom would be clearly indicated. Other applications where it is desired to identify a liquid penetrating a barrier may also be made.

While the use of cornstarch and an iodinized material have been used in the preferred embodiment, any chemical which will react in the presence of a fluid to result in a color change can be used. (e.g. Gentian violet is a colorless substance in the anhydrous state, but turns bright violet when it comes in contact with fluids such as water, blood, etc.) Cornstarch and iodinized material are safe for use in applications involving the skin, but other applications may not have such restrictions. Further, the chemicals can be selected to indicate the presence of only certain fluids by selecting materials that will react by means of a color change only in the presence of such selected fluids. The color change can also utilize a litmus type change and a P.H. dependent.

Such selection of chemicals to obtain the desired result are within the knowledge of one of ordinary skill in the art. Once the particular conditions are known, the selection of the particular chemicals to be used would be merely a matter of choice.

It is recognized that variations from the presently disclosed invention might be made which do not depart from the inventive concept of the present invention, and it is intended that such variations be considered within the inventive concept herein.

What is claimed is:

1. A pliable surgical medical glove for protecting a wearer in a surgical environment, said glove comprising:
    an outer layer formed of latex;
    an inner layer formed of latex adapted to be oriented between said outer layer and the wearer, said inner layer being laminated in part to said outer layer; and
    a generally colorless anhydrous material between said outer layer and said inner layer, said anhydrous material adapted to turn from generally colorless to colored upon being hydrated try water to indicate a breach in said outer layer of said glove.

2. The glove of claim 1, wherein said anhydrous material turns to color upon contact with blood between said outer layer and said inner layer to indicate a breach in said outer layer of said glove.

3. The glove of claim 2, wherein said anhydrous material turns to a color different than the color of blood.

4. The glove of claim 3, wherein said anhydrous material turns to violet upon contact with blood.

5. The glove of claim 2, wherein said anhydrous material is pH dependent utilizing a litmus-type appearance of color.

6. The glove of claim 2, wherein said anhydrous material also destroys viruses and bacteria contained within blood passing through such a breach in said outer layer.

7. The glove of claim 2, further comprising a second anhydrous material that turns to color upon contact with water and said generally colorless anhydrous material to indicate a breach in both of said outer and inner layers of said glove, said second anhydrous material causing a different color than that resulting from a breach in only said outer layer.

8. The glove of claim 7, wherein said second anhydrous material turns color upon contact with blood to indicate a breach in both of said outer and inner layers of said glove, said second anhydrous material causing a different color than that resulting from a breach in only said outer layer.

9. The glove of claim 1, wherein said anhydrous material turns to color upon contact with all bodily liquids between said outer layer and said inner layer to indicate a breach in said outer layer of said glove.

10. The glove of claim 9, wherein said anhydrous material also destroys viruses and bacteria contained with bodily liquids passing through such a breach in said outer layer.

11. The glove of claim 9, further comprising a second anhydrous material that turns color upon contact with water and said generally colorless anhydrous material to indicate a breach in both of said outer and inner layers of said glove, said second anhydrous material causing a different color than that resulting from a breach in only said outer layer.

12. The glove of claim 11, wherein said second anhydrous material turns color upon contact with all bodily liquids to indicate a breach in both of said outer and inner layers of said glove, said second anhydrous material causing a different color than that resulting from a breach in only said outer layer.

13. The glove of claim 1, further comprising second anhydrous material that turns color upon contact with water and said generally colorless anhydrous material to indicate a breach in both of said outer and inner layers of said glove, said second anhydrous material causing a different color than that resulting from a breach in only said outer layer.

14. The glove of claim 13, wherein said second anhydrous material turns color upon contact with blood to indicate a breach in both of said outer and inner layers of said glove, said second anhydrous material causing a different color than that resulting from a breach in only said outer layer.

15. The glove of claim 1, wherein said anhydrous material includes an iodinated material between said outer layer and said inner layer.

16. The glove of claim 15, further comprising starch applied to the surface of said inner layer directed toward the wearer.

17. The glove of claim 1, wherein said anhydrous material includes a mixture of an iodinated material and starch between said outer layer and said inner layer.

18. The glove of claim 1, further comprising a protective material covering a portion of the glove.

19. The glove of claim 18, wherein said protective material is laminated to said glove.

20. The glove of claim 18, wherein said protective material is maintained between said inner layer and said outer layer.

21. A condom for protecting a wearer, said condom comprising:
  an outer layer;
  an inner layer adapted to be oriented between said outer layer and the wearer, said inner layer being laminated in part to said outer layer, at least one of said outer and inner layers being formed of one of latex and flexible plastic; and
  a generally colorless anhydrous material between said outer layer and said inner layer, said anhydrous material adapted to turn from generally colorless to colored upon being hydrated by water to indicate a breach in said outer layer of said condom.

22. The condom of claim 21, wherein said anhydrous material turns color upon contact with all bodily liquids between said outer layer and said inner layer to indicate a breach in said outer layer of said condom.

23. The condom of claim 22, wherein said anhydrous material turns to violet.

24. The condom of claim 21, wherein said anhydrous material is pH dependent utilizing a litmus-type appearance of color.

25. The condom of claim 22, wherein said anhydrous material also destroys viruses and bacteria contained within all bodily liquid passing through such a breach in said outer layer.

26. The condom of claim 22, further comprising a second anhydrous material that turns to color upon contact with water and said generally colorless anhydrous material to indicate a breach in both of said outer and inner layers of said condom, said second anhydrous material causing a different color than that resulting from a breach in only said outer layer.

27. The condom of claim 26, wherein said second anhydrous material turns color upon contact with all bodily liquids to indicate a breach in both of said outer and inner layers of said condom, said second anhydrous material causing a different color than that resulting from a breach in only said outer layer.

28. The condom of claim 21, further comprising a second anhydrous material that turns to color upon contact with water and said generally colorless anhydrous material to indicate a breach in both of said outer and inner layers of said condom, said second anhydrous material causing a different color than that resulting from a breach in only said outer layer.

29. The condom of claim 28, wherein said second anhydrous material turns color upon contact with all bodily liquids to indicate a breach in both of said outer and inner layers of said condom, said second anhydrous material causing a different color than that resulting from a breach in only said outer layer.

30. The condom of claim 21, wherein said anhydrous material includes an iodinated material between said outer layer and said inner layer.

31. The condom of claim 21, wherein said anhydrous material includes a mixture of an iodinated material and starch between said outer layer and said inner layer.

32. A method for protecting a wearer of a pliable surgical glove, comprising the steps of:
  providing said glove comprising an outer layer formed of latex, an inner layer formed of latex adapted to be oriented between said outer layer and the wearer, said inner layer being laminated in part to said outer layer; and an anhydrous material between said outer layer and said inner layer, said anhydrous material being generally colorless prior to being hydrated;
  donning said glove; and
  inspecting said glove for the appearance of color resulting from said anhydrous material turning from generally colorless to colored upon being hydrated indicating a breach in said outer layer of said glove.

33. The method of claim 32, further comprising the step of rinsing said glove with water.

34. The method of claim 33, further comprising the step of changing the color of said glove after the rinsing step in response to water passing into said glove through a breach in said outer layer.

35. The method of claim 33, wherein the changing step includes the step of changing the color of said glove to a blue purple color.

36. The method of claim 32, wherein the providing step includes providing said glove with a second color changing material that changes color upon contact with water and said generally colorless anhydrous material to indicate a breach in both of said outer and inner layers of said glove, said second material changing to a different color than that resulting from a breach in only said outer layer; and wherein the inspecting step includes the step of inspecting said glove for a first color change indicating a breach in said outer layer of said glove and for a second color change indicating a breach in both of said outer and inner layers of said glove.

37. The method of claim 36, further comprising the step of changing the color of said glove after the rinsing step in response to water passing through a breach in both of said outer and inner layers.

38. The method of claim 37, wherein the changing step includes the step of changing the color of said glove to a color other than the color of blood.

39. The method of claim 37, wherein the changing step includes the step of changing the color of said glove to a blue purple color.

40. The method of claim 32, further comprising the step of applying a dusting of starch between said glove and the wearer prior to the donning step.

41. The method of claim 40, further comprising the step of changing the color of said glove after the rinsing step in response to water passing through a breach in both of said outer and inner layers.

42. The method of claim 41, wherein the changing step includes the step of changing the color of said glove to a color other than the color of blood.

43. The method of claim 41, wherein the changing step includes the step of changing the color of said glove to a blue purple color.

44. A pliable cover for protecting a wearer, said cover comprising:
   an outer layer;
   an inner layer adapted to be oriented between said outer layer and the wearer, said inner layer being laminated in part to said outer layer;
   first means for changing color upon contact with water between said outer layer and said inner layer to indicate a breach in said outer layer of said cover; and
   second means for changing color upon contact with water to indicate a breach in both of said outer and inner layers of said cover, said second means changing to a different color than that resulting from a breach in only said outer layer.

45. The cover of claim 44, wherein said cover is a glove.

46. The cover of claim 45, wherein said first color changing means changes color upon contact with blood between said outer layer and said inner layer to indicate a breach in said outer layer of said cover.

47. The cover of claim 46, wherein said first color changing means changes to color different than the color of blood.

48. The cover of claim 47, wherein said first color changing means changes to violet upon contact with blood.

49. The cover of claim 46, wherein said first color changing means is pH dependent utilizing a litmus-type color change.

50. The cover of claim 46, wherein said first color changing means includes the additional function of destroying viruses and bacteria passing through such a breach in said outer layer.

51. The cover of claim 44, wherein said second means changes color upon contact with blood to indicate a breach in both of said outer and inner layers of said cover.

52. The cover of claim 45, wherein said first color changing means changes color upon contact with bodily liquids between said outer layer and said inner layer to indicate a breach in said outer layer of said cover.

53. The cover of claim 52, wherein said first color changing means includes the additional function of destroying viruses and bacteria passing through such a breach in said outer layer.

54. The cover of claim 45, wherein said second means changes color upon contact with bodily liquids to indicate a breach in both of said outer and inner layers of said cover, said second means changing to a different color than that resulting from a breach in only said outer layer.

55. The cover of claim 45, wherein said first color changing means includes an iodinated material between said outer layer and said inner layer.

56. The cover of claim 55, further comprising starch applied to the surface of said inner layer directed toward the wearer.

57. The cover of claim 45, wherein said first color changing means includes a mixture of an iodinated material and starch between said outer layer and said inner layer.

58. The cover of claim 45, wherein said first color changing means includes an anhydrous iodinated material between said outer layer and said inner layer.

59. The cover of claim 45, wherein said first color changing means includes a mixture of an anhydrous iodinated material and starch between said outer layer and said inner layer.

60. The cover of claim 45, wherein at least one of said outer and inner layers is waterproof.

61. The cover of claim 45, wherein said outer and inner layers are waterproof.

62. The cover of claim 60, wherein at least one of said outer and inner layers are formed of flexible plastic material.

63. The cover of claim 61, wherein said outer and inner layers are formed of flexible plastic material.

64. The cover of claim 60, further comprising a protective material covering a portion of the cover.

65. The cover of claim 64, wherein said protective material is laminated to said cover.

66. The cover of claim 64, wherein said protective material is maintained between said inner layer and said outer layer.

67. The cover of claim 60, wherein at least one of said outer and inner layers are formed of latex.

68. The cover of claim 61, wherein said outer and inner layers are formed of latex.

69. The cover of claim 44, wherein said cover is a condom.

70. The cover of claim 69, wherein said first color changing means changes color upon contact with bodily liquids between said outer layer and said inner layer to indicate a breach in said outer layer of said cover.

71. The cover of claim 70, wherein said first color changing means changes to violet.

72. The cover of claim 69, wherein said first color changing means is pH dependent utilizing a litmus-type color change.

73. The cover of claim 70, wherein said first color changing means includes the additional function of destroying viruses and bacteria passing through such a breach in said outer layer.

74. The cover of claim 70, wherein said second means changes color upon contact with bodily liquids to indicate a breach in both of said outer and inner layers of said cover.

75. The cover of claim 69, wherein said second means changes color upon contact with blood to indicate a breach in both of said outer and inner layers of said cover.

76. The cover of claim 69, wherein said first color changing means includes an iodinated material between said outer layer and said inner layer.

77. The cover of claim 69, wherein said first color changing means includes a mixture of an iodinated material and starch between said outer layer and said inner layer.

78. The cover of claim 69, wherein said first color changing means includes an anhydrous iodinated material between said outer layer and said inner layer.

79. The cover of claim 69, wherein said first color changing means includes a mixture of an anhydrous iodinated material and starch between said outer layer and said inner layer.

80. The cover of claim 69, wherein at least one of said outer and inner layers is waterproof.

81. The cover of claim 69, wherein said outer and inner layers are waterproof.

82. The cover of claim 69, wherein at least one of said outer and inner layers are formed of flexible plastic material.

83. The cover of claim 81, wherein said outer and inner layers are formed of flexible plastic material.

84. The cover of claim 80, wherein at least one of said outer and inner layers are formed of latex.

85. The cover of claim 81, wherein said outer and inner layers are formed of latex.

86. A surgical medical glove for protecting a wearer in a surgical environment, said glove comprising:
an outer layer;
an inner layer adapted to be oriented between said outer layer and the wearer, said inner layer being laminated in part to said outer layer, at least one of said outer and inner layers being formed of latex; and
a generally colorless anhydrous material between said outer layer and said inner layer, said anhydrous material adapted to turn from generally colorless to colored upon being hydrated by all bodily liquids to indicate a breach in said outer layer of said glove.

87. The glove of claim 86, wherein said anhydrous material turns to color upon contact with blood between said outer layer and said inner layer to indicate a breach in said outer layer of said glove.

88. The glove of claim 87, wherein said anhydrous material turns to a color different than the color of blood.

89. The glove of claim 88, wherein said anhydrous material turns to violet upon contact with blood.

90. The glove of claim 86, wherein said anhydrous material is pH dependent utilizing a litmus-type appearance of color.

91. The glove of claim 87, wherein said anhydrous material also destroys viruses and bacteria contained within blood passing through such a breach in said outer layer.

92. The glove of claim 86, further comprising a second anhydrous material that turns to color upon contact with water and said generally colorless anhydrous material to indicate a breach in both of said outer and inner layers of said glove, said second anhydrous material causing a different color than that resulting from a breach in only said outer layer.

93. The glove of claim 92, wherein said second anhydrous material turns color upon contact with blood to indicate a breach in both of said outer and inner layers of said glove, said second anhydrous material causing a different color than that resulting from a breach in only said outer layer.

94. The glove of claim 86, wherein said anhydrous material also destroys viruses and bacteria contained with bodily liquids passing through such a breach in said outer layer.

95. The glove of claim 86, wherein said anhydrous material includes all iodinated material between said outer layer and said inner layer.

96. The glove of claim 95, further comprising starch applied to the surface of said inner layer directed toward the wearer.

97. The glove of claim 86, wherein said anhydrous material includes a mixture of an iodinated material and starch between said outer layer and said inner layer.

98. The glove of claim 86, further comprising a protective material covering a portion of the glove.

99. The glove of claim 98, wherein said protective material is laminated to said glove.

100. The glove of claim 98, wherein said protective material is maintained between said inner layer and said outer layer.

101. The glove of claim 86, wherein both of said outer and inner layers are formed of latex.

102. A surgical medical glove for protecting a wearer in a surgical environment, said glove comprising:
an outer layer;
an inner layer adapted to be oriented between said outer layer and the wearer, said inner layer being laminated in part to said outer layer, at least one of said outer and inner layers being formed of latex; and
a generally colorless anhydrous material between said outer layer and said inner layer, said anhydrous material adapted to turn from generally colorless to colored upon being hydrated by water and all bodily liquids to indicate a breach in said, outer layer of said glove.

103. The glove of claim 102, wherein said anhydrous material turns to color upon contact with blood between said outer layer and said inner layer to indicate a breach in said layer of said glove.

104. The glove of claim 103, wherein said anhydrous material turns to a color different than the color of blood.

105. The glove of claim 104, wherein said anhydrous material turns to violet upon contact with blood.

106. The glove of claim 102, wherein said anhydrous material is pH dependent utilizing a litmus-type appearance of color.

107. The glove of claim 103, wherein said anhydrous material also destroys viruses and bacteria contained within blood passing through such a breach in said outer layer.

108. The glove of claim 102, further comprising a second anhydrous material that turns to color upon contact with water and said generally colorless anhydrous material to indicate a breach in both of said outer and inner layers of said glove, said second anhydrous material causing a different color than that resulting from a breach in only said outer layer.

109. The glove of claim 108, wherein said second anhydrous material turns color upon contact with blood to indicate a breach in both of said outer and inner layers of said glove, said second anhydrous material causing a different color than that resulting from a breach in only said outer layer.

110. The glove of claim 102, wherein said anhydrous material also destroys viruses and bacteria contained with bodily liquids passing through such a breach in said outer layer.

111. The glove of claim 102, wherein said anhydrous material includes an iodinated material between said outer layer and said inner layer.

112. The glove of claim 111, further comprising starch applied to the surface of said inner layer directed toward the wearer.

113. The glove of claim 102, wherein said anhydrous material includes a mixture of an iodinated material and starch between said outer layer and said inner layer.

114. The glove of claim 102, further comprising a protective material covering a portion of the glove.

115. The glove of claim 114, wherein said protective material is laminated to said glove.

116. The glove of claim 114, wherein said protective material is maintained between said inner layer and said outer layer.

117. The glove of claim 102, wherein both of said outer and inner layers are formed of latex.

118. A surgical medical glove for protecting a wearer, said glove comprising:
an outer layer;
an inner layer adapted to be oriented between said outer layer and the wearer, said inner layer being laminated in part to said outer layer, at least one of said outer and inner layers being formed of latex; and a generally colorless anhydrous iodinated material between said outer layer and said inner layer, said anhydrous material being adapted to turn from generally colorless to colored upon being hydrated upon contact with water and all bodily liquids to indicate a breach in said outer layer of said glove.

119. The glove of claim 118, wherein said anhydrous material turns to color upon contact with blood between said outer layer and said inner layer to indicate a breach in said outer layer of said glove.

120. The glove of claim 119, wherein said anhydrous material turns to a color different than the color of blood.

121. The glove of claim 120, wherein said anhydrous material turns to violet upon contact with blood.

122. The glove of claim 118, wherein said anhydrous material is pH dependent utilizing a litmus-type appearance of color.

123. The glove of claim 119, wherein said anhydrous material also destroys viruses and bacteria contained within blood passing through such a breach in said outer layer.

124. The glove of claim 118, further comprising a second anhydrous material that turns to color upon contact with water and said generally colorless anhydrous material to indicate a breach in both of said outer and inner layers of said glove, said second anhydrous material causing a different color than that resulting from a breach in only said outer layer.

125. The glove of claim 124, wherein said second anhydrous material turns color upon contact with blood to indicate a breach in both of said outer and inner layers of said glove, said second anhydrous material causing a different color than that resulting from a breach in only said outer layer.

126. The glove of claim 118, wherein said anhydrous material also destroys viruses and bacteria contained with bodily liquids passing through such a breach in said outer layer.

127. The glove of claim 118, further comprising starch applied to the surface of said inner layer directed toward the wearer.

128. The glove of claim 118, wherein said anhydrous material includes a mixture of an iodinated material and starch between said outer layer and said inner layer.

129. The glove of claim 118, further comprising a protective material covering a portion of the glove.

130. The glove of claim 129, wherein said protective material is laminated to said glove.

131. The glove of claim 129, wherein said protective material is maintained between said inner layer and said outer layer.

132. The glove of claim 118, wherein both of said outer and inner layers are formed of latex.

133. A surgical medical glove for protecting a wearer, said glove comprising:

an outer layer;

an inner layer adapted to be oriented between said outer layer and the wearer, said inner layer being laminated in part to said outer layer, at least one of said outer and inner layers being formed of latex; and a mixture of a generally colorless anhydrous iodinated material and starch between said outer layer and said inner layer, said mixture adapted to turn from generally colorless to colored upon being hydrated with water and all bodily liquids to indicate a breach in said outer layer of said glove.

134. The glove of claim 133, wherein said anhydrous material turns to color upon contact with blood between said outer layer and said inner layer to indicate a breach in said outer layer of said glove.

135. The glove of claim 134, wherein said anhydrous material turns to a color different than the color of blood.

136. The glove of claim 135, wherein said anhydrous material turns to violet upon contact with blood.

137. The glove of claim 133, wherein said anhydrous material is pH dependent utilizing a litmus-type appearance of color.

138. The glove of claim 134, wherein said anhydrous material also destroys viruses and bacteria contained within blood passing through such a breach in said outer layer.

139. The glove of claim 133, further comprising a second anhydrous material that turns to color upon contact with water and said generally colorless anhydrous material to indicate a breach in both of said outer and inner layers of said glove, said second anhydrous material causing a different color than that resulting from a breach in only said outer layer.

140. The glove of claim 139, wherein said second anhydrous material turns color upon contact with blood to indicate a breach in both of said outer and inner layers of said glove, said second anhydrous material causing a different color than that resulting from a breach in only said outer layer.

141. The glove of claim 133, wherein said anhydrous material also destroys bacteria contained with bodily liquids passing through such a breach in said outer layer.

142. The glove of claim 134, further comprising starch applied to the surface of said inner layer directed toward the wearer.

143. The glove of claim 133, further comprising a protective material covering a portion of the glove.

144. The glove of claim 143, wherein said protective material is laminated to said glove.

145. The glove of claim 143, wherein said protective material is maintained between said inner layer and said outer layer.

146. The glove of claim 133, wherein both of said outer and inner layers are formed of latex.

* * * * *

UNITED STATES PATENT AND TRADEMARK OFFICE
CERTIFICATE OF CORRECTION

PATENT NO. : 6,175,962 B1
DATED : January 23, 2001
INVENTOR(S) : Gary Karlin Michelson Page 1 of 1

It is certified that error appears in the above-identified patent and that said Letters Patent is hereby corrected as shown below:

Column 4, claim 1,
Line 32, change "try" to -- by --;

Column 9, claim 95,
Line 52, change " all" to -- an --;

Column 10, claim 102,
Line 12, delete ","; and

Column 10, claim 103,
Line 16, before "layer" insert -- outer --.

Signed and Sealed this

Twenty-third Day of October, 2001

Attest:

*Nicholas P. Godici*

NICHOLAS P. GODICI
*Attesting Officer*  *Acting Director of the United States Patent and Trademark Office*